United States Patent
Bonda

(10) Patent No.: US 6,551,605 B2
(45) Date of Patent: Apr. 22, 2003

(54) DIESTERS OR POLYESTERS OF NAPHTHALENE DICARBOXYLIC ACID AS SOLUBILIZER/STABILIZER FOR RETINOIDS

(75) Inventor: Craig A. Bonda, Wheaton, IL (US)

(73) Assignee: Haarmann & Reimer (*) Notice: Subject to any disclaimer, the term of this patent is extended or adjusted under 35 U.S.C. 154(b) by 0 days.

(21) Appl. No.: 09/827,640

(22) Filed: Apr. 6, 2001

(65) Prior Publication Data
US 2002/0197285 A1 Dec. 26, 2002

(51) Int. Cl.[7] .............................. A61K 7/42; A61K 7/44; A61K 31/07; A01N 31/04
(52) U.S. Cl. .......................... 424/401; 424/59; 424/60; 514/725; 514/844; 514/970; 514/972
(58) Field of Search .................. 424/401, 59, 60; 514/725, 844, 970, 792

(56) References Cited

U.S. PATENT DOCUMENTS

| | | | |
|---|---|---|---|
| 2,607,658 A | 8/1952 | Govett et al. ................. 28/14 |
| 2,645,616 A | 7/1953 | Govett et al. ............... 252/317 |
| 2,876,163 A | 3/1959 | Garizio et al. ............... 167/90 |
| 3,239,363 A | 3/1966 | Burdge ........................ 560/80 |
| 3,255,082 A | 6/1966 | Barton ........................ 167/90 |
| 3,740,421 A | 6/1973 | Schmolka ................... 424/424 |
| 4,268,499 A | 5/1981 | Keil ............................ 424/68 |
| 4,278,655 A | 7/1981 | Elmi ........................... 424/47 |
| 4,308,328 A | 12/1981 | Salyer et al. ................ 430/17 |
| 4,350,605 A | 9/1982 | Hughett ...................... 424/47 |
| 4,383,988 A | 5/1983 | Teng et al. .................. 424/68 |
| 4,387,089 A | 6/1983 | De Polo ...................... 424/59 |
| 4,489,057 A | 12/1984 | Welters et al. .............. 424/47 |
| 4,562,067 A | 12/1985 | Hopp et al. .................. 424/59 |
| 4,673,570 A | 6/1987 | Soldati ........................ 424/66 |
| 4,725,430 A | 2/1988 | Schamper et al. ........... 424/66 |
| 4,822,602 A | 4/1989 | Sabatelli ..................... 424/65 |
| 4,990,690 A | 2/1991 | Onda et al. ................. 568/814 |
| 5,385,729 A | 1/1995 | Prencipe et al. ......... 424/70.11 |
| 5,635,166 A | 6/1997 | Galleguillos et al. ......... 424/66 |
| 5,670,140 A | 9/1997 | Deflandre et al. ........... 424/59 |
| 5,783,173 A | 7/1998 | Bonda et al. ................ 424/59 |
| 5,788,954 A | 8/1998 | Bonda et al. ................ 424/59 |
| 5,849,273 A | 12/1998 | Bonda et al. ................ 424/59 |
| 5,882,634 A | 3/1999 | Allard et al. ................ 424/59 |
| 5,976,513 A | 11/1999 | Robinson .................... 424/59 |
| 5,993,789 A | 11/1999 | Bonda et al. ................ 424/59 |
| 6,033,648 A * | 3/2000 | Candau ........................ 424/59 |
| 6,113,931 A | 9/2000 | Bonda et al. ............... 424/401 |
| 6,126,925 A | 10/2000 | Bonda et al. ................ 424/59 |
| 6,180,091 B1 | 1/2001 | Bonda et al. .............. 424/70.1 |
| 6,129,909 A1 | 10/2002 | Bonda et al. .............. 424/70.1 |

FOREIGN PATENT DOCUMENTS

| FR | 1429967 | 6/1972 |
|---|---|---|
| GB | 1277557 | 6/1972 |
| JP | 04221330 | 8/1992 |
| JP | 05310530 | 11/1993 |
| JP | 07076511 | 3/1995 |
| JP | 2001-151664 | 6/2001 |
| WO | WO 99/24256 | 5/2000 |
| WO | WO 00/57850 | 10/2000 |

OTHER PUBLICATIONS

Document No. RD 437019 A, Sep. 2000, Anonymous.*

"Photostable Cosmetic Light Screening Composition", Author: Anon. Organization, UK Publication Source, Research Disclosure (1999), 418(Feb.), P175 (No. 41803). Identifier–CODEN RSDSBB ISSN 0374–4363 Publisher Kenneth Mason Publications Ltd. Patent Information.

"Polyester And Copolyester Sheeting, Film And Structured Products Stabilized Against Degradation By Sunlight Or Other UV Light Sources", Author: Anon. Organization, Research Disclosure (1994), (Nov.), P601 (No. 36708).

(List continued on next page.)

Primary Examiner—Michael G. Hartley
Assistant Examiner—Marina Lamm
(74) Attorney, Agent, or Firm—Pendorf & Cutliff

(57) ABSTRACT

A topical composition for skin treatment comprising about 60.001% to 1% by weight of a retinoid solubilizer and/or stabilized with preferably about 0.1% to about 50% by weight of a diester or polyester of a naphthalene dicarboxylic acid having compound formula (I), (II), (III) or mixtures:

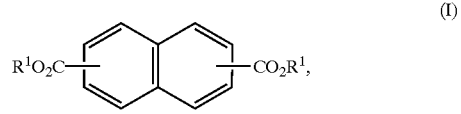

(I)

wherein $R^1$ is an alkyl group, straight chain or branched, having 1 to 22 carbon atoms;

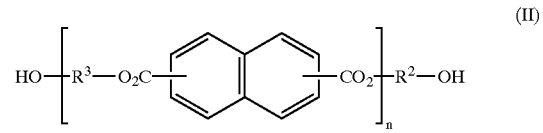

(II)

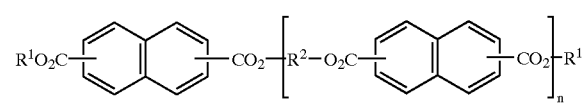

(III)

wherein each $R^1$, same or different, is an alkyl group having 1 to 22 carbon atoms, a diol having the structure HO—$R^2$—OH, or a polyglycol having the structure HO—$R^3$—(—O—$R^2$—)$_m$—OH wherein $R^2$ and $R^3$, same or different, are each an alkylene group, straight chain or branched, having 1 to 6 carbon atoms, and wherein m and n are each 1 to about 100, or a mixture thereof.

16 Claims, No Drawings

OTHER PUBLICATIONS

Fox, Charles, Fox Associates, Fair Lawn, New Jersey, "Gels and Sticks Review and Update", *Cosmetics & Toiletries*, vol. 99, Nov. 1984 (pp. 19, 20, 22, 24, 25, 28–30, 32, 34, 36, 38, 40, 42, 44, 47, 48, 50, 52, 54).

Fox, Charles, Charles Fox Associates Inc., Fair Lawn New Jersey, "Antiperspirants & Deodorants Review and Update" *Cosmetics & Toiletries*, vol. 100, Dec. 1985 (pp. 27–33, 35–36, 40–41).

"Deodorant & Antiperspirant Formulary", *Cosmetics & Toiletries*, vol. 100, Dec. 1985 (pp. 65–75).

Goldemberg, et al., "Silicones In Clear Formulations", D&CI, Feb. 1986, (pp. 34, 38, 40, 44).

STN, File Supplier, Karlsruhe, DE, File Chemical Abstracts, vol. 130, AN=158258 see the abstract XP002126186 & Research Disclosure, No. 418003, Feb. 10, 1999, p. 175 UK the whole document.

Database WPI, Section Ch, Week 200114, Derwent Publications Ltd., London, GB; Class A96, AN 2001–135326 XP002166356 Anonymous: "Cosmetic emulsions containing amino acids to prevent photochemical reactions are stabilized by addition of oils such as fatty acid esters or silicones" abstract & Research Disclosure, vol. 437, No. 019, Sep. 10, 2000 Emsworth, GB.

Zouboulis, Christos C., (Department of Dermatology, University Medical Center Benjamin Franklin, The Free University of Berlin, Berlin, Germany) "Retinoids: Is there a New Approach?", IFSCC Magazine—vol. 3, No. 3/2000, pp. 9–19.

Zatz, Joel L., "Skin Delivery of Retinoids—Reducing The Skin Irritancy of Topical Retinoids", © 1998, 1999 Joel L. Zatz (pp. 1–8) (http://www–rci.rutgers.edu/~zatz/SkinPermeation?Retinoids.html.

Weber, Fritz et al.—"Vitamin A and Retinoids", (pp. 1–3) http://www.chem.qmw.ac.uk/iubmb/newsletter/1996/news2.html; 1996.

Maddin, S. MD, et al.—"Isotretinoin improves the appearance of photodamaged skin: Results of a 36–week, multicenter, double–blind, placebo–controlled trail" *Journal Of The American Academy Of Dermatology*, Jan. 2000, Part 1 • vol. 42 • No. 1 (pp. 1–13) http://www.eblue.org/scripts/om.dll/serve . . . .

SIGMA © ProductInformation (all trans–RETINOIC ACID Sigma Prod. No. R2625 Oct. 8, 1996—ARO pp. 1–3.

Quigley, et al., "Reduced skin irritation with tretinoin containing polyolprepolymer–2, a new topical tretinoin delivery system: A sumary of preclinical and clinical investigations", Bertek Pharmaceuticals http://www.bertek.com/article_reprints/resources/skin_irritation.html Apr. 1998.

Kang, Sewon, M.D., et al., "Photoaging therapy with topical tretinoin: an evidence–based analysis", *Journal Of The American Academy Of Dermatology*, Aug. 1998, Part vol. 39 No. 2 (pp. 1–9) http://www.eblue.org/scripts/om.dll/serve . . .

Kligman, Albert M., MD, PhD., "Topical treatments for photoaged skin—separating the reality from the hype", *Postraduate Medicin: Skin Disorders Symposium: Topical treatments for photoaged skin*, vol. 102 / No. 2 / Aug. 1997 / Postgraduate Medicine p. 1–8 http://www.postgradmed.com/issues/1997/08_97/Kligman.htm.

Kligman, Albert M., MD, PhD., "The growing importance of topical retinoids in clinical dermatology: a retrospective and prospective analysis" *Journal Of The American Academy Of Dermatology*, Aug. 1998, Part 3 • Volume 39 • No. 2 (pp. 1–7). http://www.eblue.org/scripts/om.dll/serve . . . .

Hamilton, Joan O'C, "Lilly gets a Vitamin $hot from Ligan—The Retinoid Renaissance", SIGNALS Article: The Retinoid Renaissance, published Dec. 3, 1997 (pp. 1–9) http://www.signalsmag.com/signalsmag.nsf/0/665D05084647BA28825656A006B0F9D.

Moss, G.P. (World Wide Web versions prepared by)—Department of Chemistry, Queen Mary and Westfield College, United Kingdom, "Nomenclature of Retinoids—Recomendations 1981)", International Union Of Pure And Applied Chemistry And International Union Of Biochemistry And Molecular Biology, IUPAC–IUB Joint Commission On Biochemical Nomenclature (JCBN) pp. 1–10 http://www.chem.qmw.ac.uk/iupac/misc/ret.html; 1981.

"Retinoids", *Molecular Medicine—News from Research Laboratories*—pp. 1–2 http://www.aston.it/biomedicine/biom0054.htm Dec. 1997.

* cited by examiner

DIESTERS OR POLYESTERS OF NAPHTHALENE DICARBOXYLIC ACID AS SOLUBILIZER/STABILIZER FOR RETINOIDS

FIELD OF THE INVENTION

The present invention is directed to diester and polyester compounds for use as solubilizers and stabilizers of retinoids and methods of solubilizing and stabilizing retinoids. The diesters or polyesters of naphthalene dicarboxylic acids facilitate the delivery of the retinoids to the skin more efficiently and in a more aesthetically pleasing and less irritating manner than the organic solvents presently used, e.g., ethanol or isopropyl myristate. The present invention is directed to the use of diesters or polyesters of naphthalene dicarboxylic acids which are surprisingly effective at solubilizing the retinoids and stabilizing them such that they remain biologically active and, therefore, therapeutically effective for longer periods of time. Once solubilized in diesters or polyesters of one or more naphthalene dicarboxylic acids, the retinoids may be incorporated in topical preparations which have superior spreadability, emolliency, and skin feel and are surprisingly effective at delivering the retinoids to the skin such that they may be more biologically active, less irritating and, therefore, therapeutically more effective.

BACKGROUND OF THE INVENTION AND PRIOR ART

Retinoids are a class of compounds consisting of four isoprenoid units joined in a head to tail manner. All retinoids may be derived from a monocyclic parent compound containing five carbon-carbon double bonds and a functional group at the terminus of the acyclic portion (see structure below). The retinoids include Vitamin A (retinol) and its derivatives, analogues, and metabolites, both natural and synthetic, that exhibit biological activity qualitatively similar to retinol. Of particular interest to this invention are retinol, retinyl esters, retinal, and isomers of retinoic acid, including all-trans-retinoic acid (tretinoin) and cis-isomeric retinoic acids, e.g., 13-cis-retinoic acid (isotretinoin) and 9-cis-retinoic acid. The naturally occurring retinoids are essential for many of life's processes including vision, reproduction, metabolism, differentiation, bone development, and pattern formation during embryogenesis. Retinoids comprise an important class of drugs used to treat a variety of health conditions including acne, photoaging, psoriasis, ichthyosis, hair loss, and various cancers.

It is convenient to omit the explicit representation of C and H atoms in the skeletal formulae of retinoids as follows:

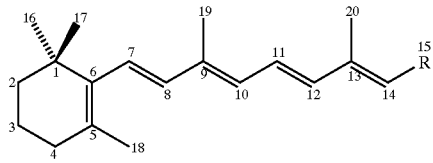

wherein R is selected from the group consisting of (1)–(10), as follows:

(1) $CH_2OH$
(2) CHO
(3) $CO_2H$
(4) $CH_3$
(5) $CH_2OCOCH_3$
(6) $CH_2NH_2$
(7) CH=NOH
(8) CH=N$[CH_2]_4$CHNH$_2CO_2H$
(9) $CO_2C_2H_5$; and (10)

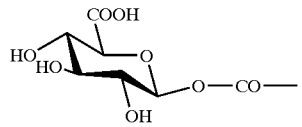

Retinoids are lipophilic. For example, tretinoin is practically insoluble in water, slightly soluble in ethanol (3 mg/ml) and chloroform, sparingly soluble in ether, and soluble in methylene chloride and dimethyl sulfoxide (40 mg/ml). Surprisingly, it has been found that diesters of naphthalene dicarboxylic acid are unexpectedly good solvents for retinoids. For example, isotretinoin is soluble in the diethylhexyl diester of 2,6-naphthalene-dicarboxylic acid (diethylhexyl 2,6-naphthalate, HallBrite TQ, C. P. Hall) at approximately 6.7 mg/ml, and tretinoin is soluble in the same diester at approximately 5.6 mg/ml.

Owing to their high degree of unsaturation, retinoids are extremely sensitive to UV light, air, and oxidizing agents. For example, tretinoin should be stored under an atmosphere of inert gas (e.g., argon) in the dark at <−20° C. to preserve its integrity and biological activity. While solutions of tretinoin in pure organic solvents are stable when stored in the dark, aqueous solutions deteriorate quickly. Diesters of naphthalene dicarboxylic acid are organic in nature and extremely hydrophobic. Therefore, a solution of a retinoid such as tretinoin or isotretinoin in a diester of naphthalene dicarboxylic acid is expected to be quite stable if kept in the dark.

Commercially available preparations of retinoids typically contain ethanol in high concentrations (e.g., 55%) as the retinoid solvent. Topically applied retinoids such as tretinoin and isotretinoin are known to be quite irritating to the point where patients often discontinue therapy because the imitation becomes intolerable. Studies have indicated that the degree of irritation is dose-dependent; i.e., 0.1% isotretinoin is more irritating than 0.025% isotretinoin. This high degree of irritation has been linked to the propensity of ethanol and its solutes to be rapidly absorbed into the skin, penetrating through the epidermis and deeply into and through the dermis, resulting in an initially high and irritating concentration of retinoid. Unfortunately, studies have found that therapeutic effectiveness is also dose-dependent; i.e., 0.1% isotretinoin is more effective than 0.025% isotretinoin. Thus, patients are often faced with the unpleasant situation of choosing between optimal therapeutic effectiveness on the one hand, and low and tolerable irritation on the other.

In accordance with the present invention retinoids, such as isotretinoin, dissolved in diesters or polyesters of naphthalene dicarboxylic acid, such as diethylhexyl 2,6-naphthalate, diffuse more slowly into the skin penetrating less deeply, thereby lessening skin irritation.

Topical retinoid preparations made with diesters or polyesters of naphthalene dicarboxylic acid, such as diethylhexyl 2,6-naphthalate, are more emollient and cosmetically elegant, with a superior skin feel to other retinoid preparations. This in turn contributes to improved patient compliance because patients are more likely to apply preparations that feel good to them.

SUMMARY OF THE INVENTION

In accordance with the present invention, it has been found that diesters and/or polyesters of one or more naphthalene dicarboxylic acids can be used as a solubilizer and/or stabilizer for retinoids. Compositions containing one or more retinoids together with one or more diesters or polyesters of naphthalene dicarboxylic acids are unexpectedly less irritating and effective for topical application to skin, as a therapeutic skin enhancer.

The retinoid solubilizing/stabilizing compounds of the present invention are diesters and/or polyesters of a naphthalene dicarboxylic acid. The diesters and polyesters are reaction products of (a) a naphthalene dicarboxylic acid having the structure:

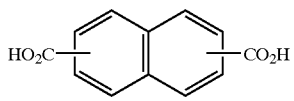

and (b) an alcohol having the structure $R^1$—OH, or a diol having the structure HO—$R^2$—OH, or a polyglycol having the structure HO—$R^3$—(—O—$R^2$—)$_m$—OH, wherein $R^1$ is an alkyl group, straight chain or branched, having 1 to 22 carbon atoms, $R^2$ and $R^3$, same or different, are each an alkylene group, having 1 to 6 carbon atoms, and wherein m and n are each 1 to about 100, preferably 1 to about 10, more preferably 2 to about 7, or a mixture thereof.

A diester of the present invention has the structure (I):

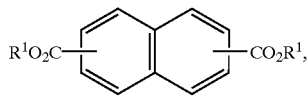

wherein $R^1$ is an alkyl group, straight chain or branched, having 1 to 22 carbon atoms.

The diesters and polyesters of naphthalene dicarboxylic acids of the present invention also may have the general formula (II):

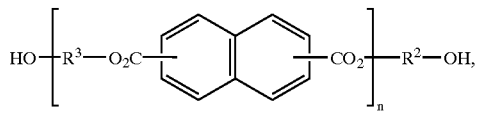

wherein $R^2$ and $R^3$, same or different, are each an alkylene group having 1 to 6 carbon atoms, and n=1 to about 100, preferably 1 to about 10, more preferably 2 to about 7.

Alternatively, the diesters and polyesters of the present invention can be end-capped with an alcohol or an acid. The end-capped polyesters have the structural formula (III):

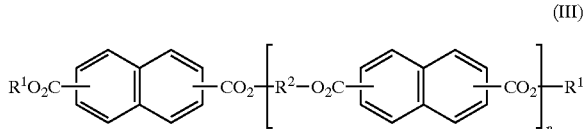

wherein each $R^1$, same or different, is an alkyl group having 1 to 22 carbon atoms, or a diol having the structure HO—$R^2$—OH, or a polyglycol having the structure HO—$R^3$—(—O—$R^2$—)$_m$—OH, and, wherein $R^2$ and $R^3$, same or different, are each an alkylene group, straight chain or branched, having 1 to 6 carbon atoms, wherein m and n are each 1 to about 100, preferably 1 to about 10, more preferably 2 to about 7, or a mixture thereof.

These diesters and polyesters are known UV absorbents and stabilizers for a dibenzoylmethane derivative, such as PARSOL® 1789, as disclosed in this assignee's U.S. Pat. Nos. 5,993,789; 6,180,091; 6,129,909; 6,113,931; and 6,126,925, hereby incorporated by reference.

The preferred diesters and polyesters of the present invention have a weight average molecular weight of about 244 to about 4000, and more preferably about 400 to about 1500. To achieve the full advantage of the present invention, the diester or polyester has a weight average molecular weight of about 440 to about 1000.

The naphthalene dicarboxylic acid is selected from the group consisting of 1,2-naphthalene dicarboxylic acid; 1,3-naphthalene dicarboxylic acid; 1,4-naphthalene dicarboxylic acid; 1,5-naphthalene dicarboxylic acid; 1,6-naphthalene dicarboxylic acid; 1,7-naphthalene dicarboxylic acid; 1,8-naphthalene dicarboxylic acid; 2,3-naphthalene dicarboxylic acid; 2,6-naphthalene dicarboxylic acid; 2,7-naphthalene dicarboxylic acid, and mixtures thereof. Preferred dicarboxylic acids are the 2,6-, 1,5- and 1,8-naphthalene dicarboxylic acids.

The alcohol $R^1$—OH can be, for example, methanol, ethanol, propanol, isopropyl alcohol, n-butanol, sec-butanol, isobutyl alcohol, tert-butyl alcohol, amyl alcohol, 1-hexanol, 1-octanol, 1-decanol, isodecyl alcohol, 1-undecanol, 1-dodecanol, 1-tridecyl alcohol, 1-tetradecanol, 1-hexadecanol, 1-octadecanol, 1-eicosonol, 1-decosonol, 2-ethylhexyl alcohol, 2-butyloctanol, 2-butyldecanol, 2-hexyldecanol, 2-octyldecanol, 2-hexyldodecanol, 2-octyldodecanol, 2-decyltetradecanol, and mixtures thereof.

The glycol or polyglycol can be, for example, ethylene glycol, propylene glycol, 1,2-propanediol, diethylene glycol, triethylene glycol, tetraethylene glycol, dipropylene glycol, tripropylene glycol, methyl propanediol, 1,6-hexanediol, 1,3-butanediol, 1,4-butanediol, PEG-4 through PEG-100, PPG-9 through PPG-34, pentylene glycol, neopentyl glycol, trimethylpropanediol, 1,4-cyclohexanedimethanol, 2,2-dimethyl-1,3-propanediol, 2,2,4,4-tetramethyl-1,3-cyclobutanediol, and mixtures thereof.

Surprisingly, these diesters and polyesters of naphthalene dicarboxylic acids are quite effective as solubilizers and stabilizers for topical application of retinoids to the skin, while providing the user with sunscreen protection, when contained in a composition in an amount of at least about 0.1% by weight, up to about 50% by weight, preferably about 0.2% to 30% by weight, more preferably about 10% to 20% by weight, based on the total weight of a composition containing one or more retinoids.

Accordingly, one aspect of the present invention is to provide a solvent/solubilizer for retinoids for topical application of retinoids, said solvent/stabilizer comprising 0.1% by weight to about 50% by weight, based on the total weight of a composition containing one or more retinoids, wherein the solvent/stabilizer comprises a diester or polyester of a naphthalene dicarboxylic acid.

Another aspect of the present invention is to provide a solubilizer/stabilizer for retinoids that also provides UV sunscreen protection and reduces the irritation to human skin resulting from topical application of retinoids.

Still another aspect of the present invention is to provide an organic solvent for retinoids capable of being emulsified together with water, such that one or more water-soluble, moisturizing components can be added to the emulsion to provide an oil-in-water or water-in-oil emulsion that reduces the irritation associated with skin contact by retinoids.

The above and other aspects and advantages of the present invention will become more apparent from the following detailed description of the preferred embodiments.

DETAILED DESCRIPTION OF THE PREFERRED EMBODIMENTS

The preferred compositions of the present invention include a retinoid, including all derivatives of retinol, its analogous, and metabolites, both natural and synthetic, that exhibit biological activity qualitatively similar to retinol, in an amount of about 0.001% to about 1% by weight, preferably about 0.01% to about 0.1% by weight, and about 0.1% to 99.999%, preferably about 0.1% to about 50%, by weight of the composition, of a diester or polyester of naphthalene dicarboxylic acid having formula (I), (II) or (III).

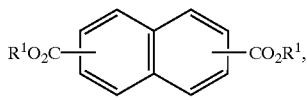
(I)

wherein $R^1$ is an alkyl group, straight chain or branched, having 1 to 22 carbon atoms;

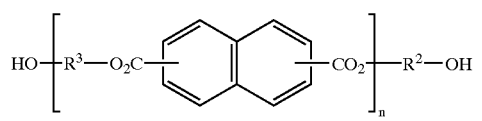
(II)

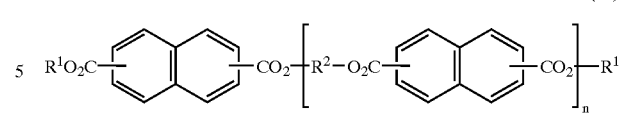
(III)

wherein each $R^1$, same or different, is an alkyl group having 1 to 22 carbon atoms, or a diol having the structure HO—$R^2$—OH, or a polyglycol having the structure HO—$R^3$—(—O—$R^2$—)$_m$—OH, and, wherein $R^2$ and $R^3$, same or different, are each an alkylene group, straight chain or branched, having 1 to 6 carbon atoms, wherein m and n are each 1 to about 100, preferably 1 to about 10, more preferably 2 to about 7, or a mixture thereof.

The preferred retinoids that are stabilized/solubilized with the diesters or polyesters of naphthalene dicarboxylic acids, in accordance with the present, invention, include retinol; retinol palmitate; retinaldehyde; tretinoin (all-trans retinoid acid); retinol palmitate; retinoic acid, isotretinoin (13-cis retinoic acid); alitretinoin (9-cis retinoic acid); motretinide; adapalene; tazarotene; tazaroteinic acid; istretinoin; etretinate; acitretin; all-trans acitretin; 11-cis, 13-cis-12-hydroxymethyl retinoic acid, δ-lactone; all-trans retinoyl β-glucuronide; tamibarotene (Am-80); arotinoids; LGD 1069; fenretinide [N-(4-hydroxy-phenyl)-retinamide]; E 5166 (polyprenoic acid); CD 2398; mefarotene (Ro 40-8757); and mixtures thereof.

The following formula exemplifies the use of diethylhexyl 2,6-naphthalate as a solvent and emollient in a 0.1% isotretinoin preparation.

EXAMPLE 1
0.1% Isotretinoin Topical Treatment For Sun-Damaged Skin

This light, pleasant gel delivers the maximum therapeutic dose of isotretinoin in a moisturizing, emollient base. Emolliency and solvency for the isotretinoin is provided by HallBrite® TQ (diethylhexyl 2,6-naphthalate).

| Phase | INCI/CTFA Chemical Name | Trade Name, Supplier | Preferred % w/w | Range % w/w | Preferred Range % w/w |
|---|---|---|---|---|---|
| A. | Diethylhexyl 2-6-naphthalate | HallBrite TQ, C. P. Hall | 16.00 | 0.1–99.999 | 1–20 |
|  | Isododecane | Permethyl 99a, Presperse | 6.00 | 0–15 | 0.5–10 |
|  | Shea Butter | Shea butter, Ultra | 1.00 | 0–2 | 0.5–1.5 |
|  | Tocopherol | Vitamin E 6-100, Eastman | 0.14 | 0–1.4 | 0.03–0.2 |
|  | Butylated hydroxytoluene | BHT, Aldrich | 0.05 | 0–0.1 | 0.01–0.1 |
|  | Isotretinoin | 13-cis-retinoic acid, Aldrich | 0.10 | 0.001–1 | 0.025–0.1 |
|  | Polyacrylamide & C13–14 Isoparaffin & Laureth-7 | Sepigel 305, Seppic | 2.50 | 0–5 | 1–3 |
| B. | Water | Deionized Water | Q.S. | 0–90 | 25–80 |
|  | Methylpropanediol | MPDiol, Lyondell | 4.00 | 0–10 | 2–6 |
|  | Glycerin | Glycerin USP, C. P. Hall | 2.00 | 0–10 | 1–6 |
|  | Allantoin | Allantoin, ISP | 0.10 | 0–3 | 0.05–2 |
|  | Preservative, such as, Propylene glycol & Diazolindinyl urea & Methylparaben & Propylparaben | Germaben II, ISP | 1.00 | 0–5 | 0.1–2 |
| C. | Cyclomethicone | DC 345 Fluid, Dow Corning | 1.00 | 0–20 | 0.2–10 |
|  | Yeast extract | Biodynes TRG, Brooks | 1.00 | 0–5 | 0.1–4 |

Procedure (Entirely at Room Temperature)
1. Oil phase: In main vessel, combine diethylhexyl 2,6-naphthalate, isododecane, and tocopherol. Add isotretinoin and stir until dissolved. Add Shea butter and BHT and stir until dissolved. (NOTE: temperature may be raised to 50° C. to speed dissolution.) Add Sepigel and blend with sweep stirring until homogeneous.
2. Water Phase: In separate vessel, blend "B " additives and stir to dissolve Allantoin.
3. With sweep stirring, slowly add Water Phase to Oil Phase. Stir to smooth white gel.
4. Add cyclomethicone and yeast extract. Stir until fully incorporated.

The following formula exemplifies the use of diethylhexyl 2,6-naphthalate as an emollient and solvent for tretinoin.

EXAMPLE 2

0.1% Tretinoin Creme Topical Treatment For Sun-Damaged Skin

This creamy emulsion delivers the maximum therapeutic dose of tretinoin in a moisturizing, emollient base. Emolliency and solvency for the tretinoin is provided by Hall-Brite® TQ (diethylhexyl 2,6-naphthalate).

| Phase | INCI/CTFA Chemical Name | Trade Name, Supplier | Preferred % w/w | Range % w/w | Preferred Range % w/w |
|---|---|---|---|---|---|
| A. | Diethylhexyl 2,6-naphthalate | HallBrite TQ, C. P. Hall | 19.00 | 0.1–50 | 1–20 |
| | Isododecane | Permethyl 99a, Presperse | 6.00 | 0–15 | 0.5–10 |
| | Shea Butter | Shea butter, Ultra | 1.00 | 0–2 | 0.5–1.5 |
| | Tocopherol | Vitamin E 6-100, Eastman | 0.14 | 0–1.4 | 0.03–0.2 |
| | Butylated hydroxytoluene | BHT, Aldrich | 0.05 | 0–0.1 | 0.01–0.1 |
| | Tretinoin | All-trans-retinoic acid, Aldrich | 0.10 | 0.001–1 | 0.025–0.1 |
| | Behenyl Alcohol & Glyceryl Stearate & Glyceryl Stearate Citrate & Sodium Dicocoylethylenediamine PEG-15 Sulfate | Ceralution H, Condea Vista | 3.00 | 0–10 | 0.5–5 |
| B. | Water | Deionized Water | Q.S. | 0–90 | 25–80 |
| | Methylpropanediol | MPDiol, Lyondell | 4.00 | 0–10 | 2–6 |
| | Glycerin | Glycerin USP, C. P. Hall | 2.00 | 0–10 | 1–6 |
| | Allantoin | Allantoin, ISP | 0.10 | 0–3 | 0.05–2 |
| C. | Preservative, such as, Propylene glycol & Diazolindinyl urea & Methylparaben & Propylparaben | Germaben II, ISP | 1.00 | 0–5 | 0.1–2 |
| | Polyacrylamide & C13–14 Isoparaffin & Laureth-7 | Sepigel 305, Seppic | 3.00 | 0–5 | 1–3 |
| | Cyclomethicone | DC 345 Fluid, Dow Corning | 1.00 | 0–20 | 0.2–10 |

Procedure
1. Oil Phase: In main vessel, combine diethylhexyl 2,6-naphthalate, isododecane, tocopherol and BHT. Add isotretinoin and stir until dissolved. (NOTE: temperature may be raised to 50° C. to speed dissolution.) Add Shea butter and stir until dissolved. Raise temperature to 65° C. Add ceralution H and stir until dissolved.
2. Water Phase: In separate vessel, blend "B" additives and stir to dissolve Allantoin. Heat to 65° C.
3. While homogenizing, add oil phase to water phase. Homogenize for one minute.
4. Remove from heat. Switch to sweep stirring. When temperature falls below 45° C., add Germaben II, then Sepigel and stir to homogeneous creme. Lastly, add cyclomethicone with stirring.

While the invention has been described in detail in the foregoing description, the same is to be considered as illustrative and not restrictive in character, it being understood that the scope of the invention includes changes and modifications to the preferred embodiment described within the spirit and scope of the invention.

What is claimed is:

1. A composition comprising about 0.001% to about 1% of a retinoid, and about 0.1% by weight of a diester or polyester of naphthalene dicarboxylic acid selected from the group consisting of formula (I), formula (II), formula (III) and mixtures thereof:

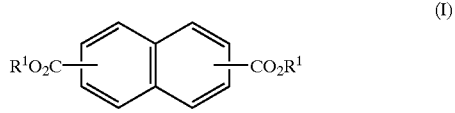

wherein each $R^1$, same or different, is an alkyl group, straight chain or branched, having 1 to 22 carbon atoms;

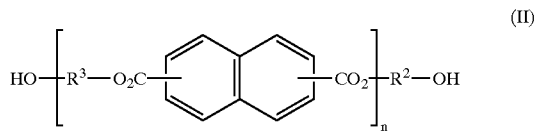

-continued

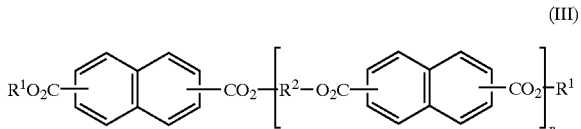

wherein each $R^1$ of formula III, same or different, is selected from the group consisting of an alkyl group having 1 to 22 carbon atoms; a diol having the structure HO—$R^2$—OH; and a polyglycol having the structure HO—$R^3$—(—OO$R^2$—)$_m$—OH, wherein $R^2$ and $R^3$, same or different, are each an alkylene group, straight chain or branched, having 1 to 6 carbon atoms, and wherein m and n are each in the range of 1 to about 100, or a mixture thereof.

2. A composition in accordance with claim 1, wherein the diester or polyester compound is included in the composition in an amount of about 0.2% to about 30% by weight of the composition.

3. A composition in accordance with claim 1, wherein the diester or polyester compound is a diester or polyester of 2,6-naphthalene dicarboxylic acid.

4. A method of delivering a retinoid topically to skin comprising mixing with the retinoid about 0.1% to 99.999% by weight to form a composition, wherein the percentage is based on the total weight of the composition, of a diester or polyester of a naphthalene dicarboxylic acid stabilizing compound selected from the group consisting of formula (I), formula (II), formula (III) and mixtures thereof:

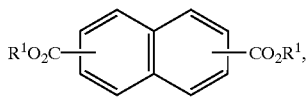

(I)

wherein $R^1$ is an alkyl group, straight chain or branched, having 1 to 22 carbon atoms;

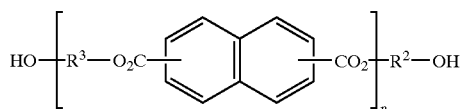

(II)

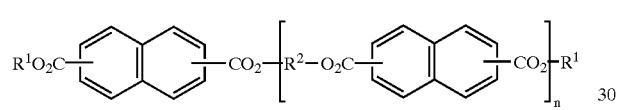

(III)

wherein each $R^1$, same or different, is selected from the group consisting of an alkyl group having 1 to 22 carbon atoms; a diol having the structure HO—$R^2$—OH; and a polyglycol having the structure HO—$R^3$—(—O—$R^2$—)$_m$—OH, wherein $R^2$ and $R^3$, same or different, are each an alkylene group, straight chain or branched, having 1 to 6 carbon atoms, and wherein m and n are each in the range of 1 to about 100, or a mixture thereof; and then applying the composition topically to skin.

5. A method in accordance with claim 4, wherein the diester or polyester of a naphthalene dicarboxylic acid is included in the composition in an amount in the range of about 0.1% to about 50% by weight.

6. A method in accordance with claim 5, wherein the diester or polyester of a naphthalene dicarboxylic acid is included in the composition in an amount in the range of about 1% to about 20% by weight.

7. A method in accordance with claim 4, wherein the diester is the diethylhexyl ester of naphthalene dicarboxylic acid.

8. A method in accordance with claim 7, wherein the diester is diethylhexyl 2,6-naphthalate.

9. A method in accordance with claim 4, wherein the retinoid is:

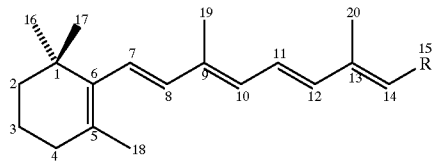

wherein R is selected from the group consisting of (1)–(10), as follows:

(1) $CH_2OH$
(2) CHO
(3) $CO_2H$
(4) $CH_3$
(5) $CH_2OCOCH_3$
(6) $CH_2NH_2$
(7) CH=NOH
(8) CH=N[$CH_2$]$_4$CHNH$_2$CO$_2$H
(9) $CO_2C_2H_5$; and

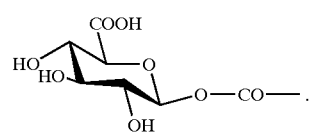

(10)

10. A method in accordance with claim 9, wherein the retinoid is selected from the group consisting of isotretinoin, tretinoin, and mixtures thereof.

11. A composition in accordance with claim 1, wherein the retinoid is:

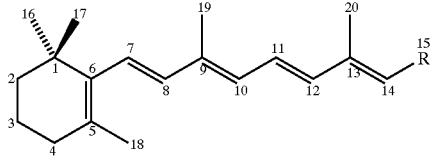

wherein R is selected from the group consisting of (1)–(10), as follows:

(1) $CH_2OH$
(2) CHO
(3) $CO_2H$
(4) $CH_3$
(5) $CH_2OCOCH_3$
(6) $CH_2NH_2$
(7) CH=NOH
(8) CH=N[$CH_2$]$_4$CHNH$_2$CO$_2$H
(9) $CO_2C_2H_5$; and

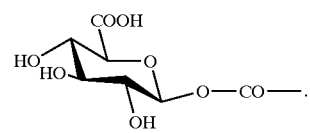

(10)

12. A composition in accordance with claim 11, wherein the retinoid is selected from the group consisting of isotretinoin, tretinoin, and mixtures thereof.

13. A composition in accordance with claim 1, wherein the retinoid is selected from the group consisting of retinoids that are stabilized/solubilized with the diesters or polyesters of naphthalene dicarboxylic acids.

14. A composition in accordance with claim 13, wherein the retinoid is selected from the group consisting of retinol, retinol palmitate, retinaldehyde, tretinoin (all-trans retinoic acid), retinoic acid, isotretinoin (13-cis retinoic acid), alitretinoin (9-cis retinoic acid), motretinide, adapalene, tazarotene, tazarotenic acid, istretinoin, etretinate, acitretin, all-trans retinoyl β-glucuronide, tambarotene (Am-80), arotinoids, LGD 1069, fenretinide [N-(4-hydroxy-phenyl)- retinamide], E 5166 (polyprenoic acid), CD 2398, mefarotene (Ro 40-8757) and mixtures thereof.

15. A composition in accordance with claim 14, wherein the retinoid is retinol palmitate.

16. A method in accordance with claim 4, wherein the retinoid is retinol palmitate.

* * * * *